United States Patent [19]

Sherwood et al.

[11] Patent Number: 5,044,031
[45] Date of Patent: Sep. 3, 1991

[54] PASSIVE REWARMING ARTICLES

[75] Inventors: John J. Sherwood, Beloit, Ohio; David L. Thibodeau, 11662 Sharonwoods Ct., Cincinnati, Ohio 45241; Philip R. Foster, 522 N. Greenlawn Ave., South Bend, Ind. 46617

[73] Assignees: Philip R. Foster, Cincinnati, Ohio; David L. Thibodeau, South Bend, Ind.

[21] Appl. No.: 895,723

[22] Filed: Aug. 12, 1986

[51] Int. Cl.$^5$ .............................................. A61G 1/01
[52] U.S. Cl. ........................................... 5/481; 2/69; 2/69.5; 5/82 R; 5/420
[58] Field of Search ............... 128/373, 379, 399, 402; 2/69, 69.5, 70; 5/82 R, 420, 481

[56] References Cited

U.S. PATENT DOCUMENTS

| 218,420 | 8/1879 | Baker . | |
| 965,921 | 8/1910 | Mercey | 2/69 |
| 1,158,834 | 11/1915 | Parker | 128/402 |
| 1,373,378 | 3/1921 | Backmann . | |
| 1,678,125 | 7/1928 | Petrescu | 2/69.5 |
| 2,227,751 | 1/1941 | Idelman | 2/84 |
| 2,657,387 | 11/1953 | Ketcham | 2/69.5 |
| 3,096,759 | 7/1963 | Coolbaugh | 128/94 |
| 3,624,848 | 12/1971 | Nissen | 5/420 |
| 3,714,947 | 2/1973 | Hardy | 128/400 |
| 3,739,399 | 6/1973 | Sheahon | 2/69.5 |
| 3,801,420 | 4/1974 | Anderson | 161/52 |
| 3,854,156 | 12/1974 | Williams | 5/347 |
| 4,124,908 | 11/1978 | Burns et al. | 2/69.5 |
| 4,178,637 | 12/1979 | Wrightson | 2/69.5 |
| 4,329,747 | 5/1982 | Russell | 5/420 |
| 4,347,629 | 9/1982 | Itoi | 2/69.5 |
| 4,375,111 | 3/1983 | Hall | 5/420 |
| 4,513,461 | 4/1985 | Tardivel | 2/69.5 |
| 4,535,495 | 8/1985 | Oldfield | 5/461 |
| 4,579,753 | 4/1986 | Gjendemsjo | 2/69.5 |
| 4,605,582 | 8/1986 | Silas et al. | 5/436 |

FOREIGN PATENT DOCUMENTS

| 2124627 | 11/1972 | Fed. Rep. of Germany | 5/420 |
| 1443600 | 7/1976 | United Kingdom | 5/420 |
| 2087224A | 5/1982 | United Kingdom . | |

Primary Examiner—Michael Safavi
Attorney, Agent, or Firm—Charles R. Wilson

[57] ABSTRACT

A passive rewarming article for use with traumatized individuals, e.g. those victims suffering from hypothermia, shock, or expsure is made from a closed-cell foam material. The preferred rewarming article comprises a body portion, at least one independent side flap, a foot flap, and a detachable head pocket. The rewarming article is enconomical to construct, yet provides high body heat retention capability under both wet and dry conditions.

20 Claims, 4 Drawing Sheets

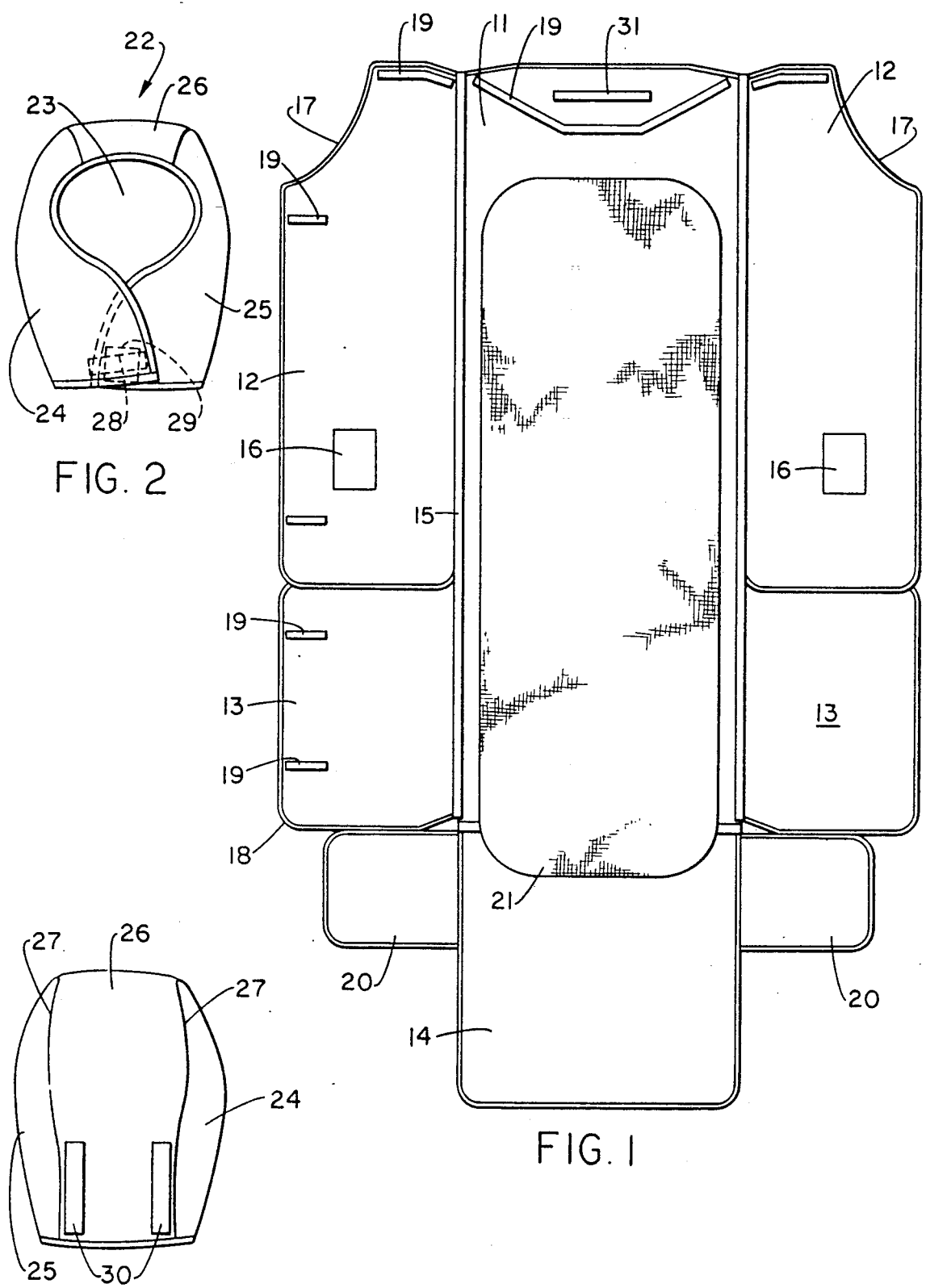

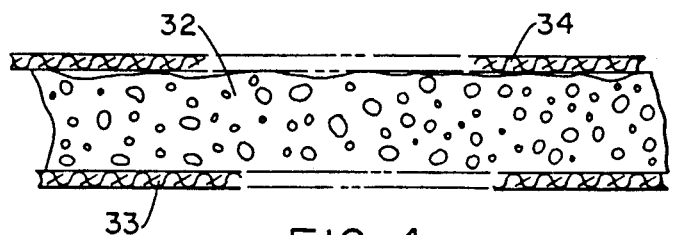
FIG. 4
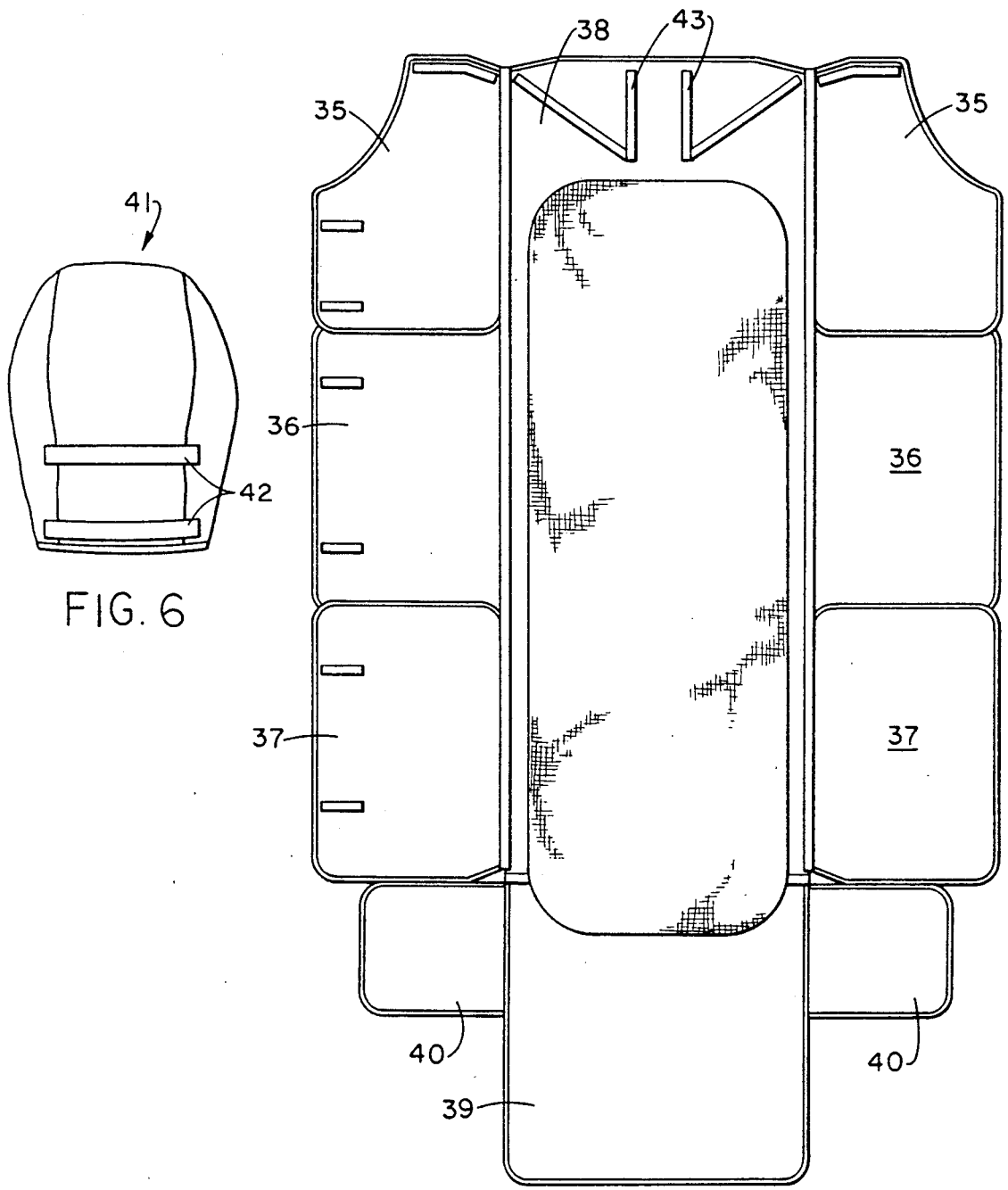
FIG. 6
FIG. 5

PASSIVE REWARMING ARTICLES

This invention relates to passive rewarming articles. More particularly, the invention relates to rewarming articles which are made of a material particularly adapted for the article's end use.

Excessive environmental exposure by warm-blooded animals can bring on shivering and eventually hypothermia. Hypothermia is a condition whereby the body temperature drops dramatically. In fact, the temperature can drop to the point where it is life threatening. The body experiences such a condition primarily after prolonged exposure to the elements, e.g. submersion in icy waters or extended time in the bitter cold. Anyone suffering from hypothermia must be quickly attended to before irreversible body damage or even death occurs. An obvious cure to the problem is to raise the body temperature of the individual. It has long been known that a person suffering from hypothermia should be wrapped in a blanket. The effect of the blanket is to retain body heat; thereby gradually warming the body.

Shock is another life threatening condition experienced by accident victims. For example, excessive bleeding can cause the human body to go into shock. A known method of alleviating such a condition includes the wrapping of the victim in a blanket. This has the effect of gradually warming the body by the retention of body heat.

Various articles have been developed for use specifically on victims suffering from exposure, hypothermia, or shock. Such articles are especially constructed for use by professionally trained emergency survival teams. For example, life squads and paramedics in the military have been issued thermal recovery bags for use in their work. Such bags basically operate on the same principle as a blanket. They are for the purpose of retaining the body heat of the victim. Naturally, the better the insulating value of the blanket or recovery bag the better it will perform its heat retention function. U.S. Pat. No. 3,096,759 to Richard W. Coolbaugh is one example of a thermal recovery wrapper. The disclosed wrapper is made of a plastisol saturated nylon scrim with polyurethane foam pads.

While the problem of hypothermia and shock are widely experienced and various attempts have been made to treat victims suffering from these conditions, there is still a need for a an improved product. Products of the prior art are deficient in that they do not effectively retain body heat or the articles especially made for such purposes suffer in one or more ways; for example, cost of construction, strength of materials, bulkiness, weight, and ease of transporting the victim. Of particular importance is the fact prior art articles tend to lose their rewarming effectiveness when wetted. That is, water which is found on the victim's clothing or body fluids will significantly affect the performance of prior known recovery articles. Such a wet condition is commonly experienced and, therefore, articles made of materials which have inadequate wet insulation characteristics will be deficient in an important respect.

There has now been developed passive rewarming articles for use with accident victims, for example, victims suffering from exposure, hypothermia, or shock. The rewarming article is constructed of a special material which effectively retains heat in a wet or dry environment. This characteristic thereby insures that maximum efficiency of body heat retention is achieved in a variety of environmental conditions likely to be encountered. Additionally, the construction of the article is such that it is economical to produce, has the required strength, and provides various features deemed necessary by emergency survival teams.

SUMMARY OF THE INVENTION

A passive rewarming article for use with accident victims is constructed from a closed-cell foam material The rewarming article preferably comprises a body portion, at least one independent foldable side flap on each side of the body portion, a foldable foot flap, and a detachable head pocket. The side flaps allow access to the victim for emergency manipulative functions, yet do not permit a substantial loss of body heat. The head pocket is dimensioned to slip over the victim's head and additionally has a cutout for exposure of at least the victim's eyes.

BRIEF DESCRIPTION OF THE DRAWINGS

FIG. 1 is a front view of a passive rewarming article of this invention.

FIG. 2 is a front view of a detachable head pocket for use with the rewarming article of FIG. 1.

FIG. 3 is a back view of the head pocket of FIG. 2.

FIG. 4 is a partial cross section of the material used in constructing the rewarming article of FIG. 1.

FIG. 5 is a front view of another passive rewarming article illustrating the use of three side flaps per side.

FIG. 6 is a back view of a detachable head pocket for use with the rewarming article of FIG. 5.

DETAILED DESCRIPTION OF THE INVENTION

Figure 7:
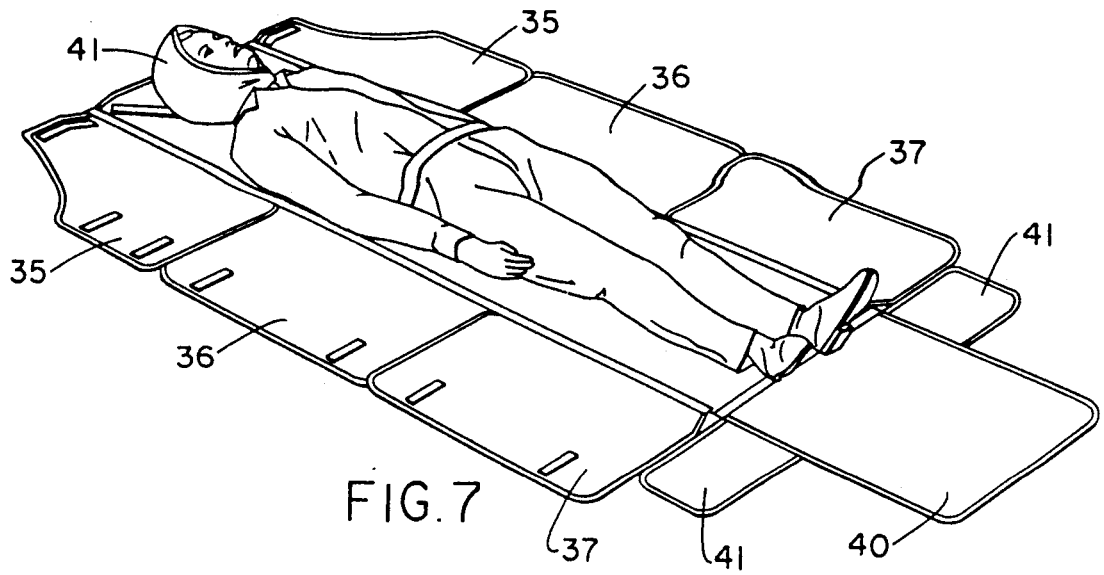
FIGS. 7-9 are views in perspective of the rewarming article showing its use with a victim.

Passive rewarming articles of this invention are constructed from a closed-cell foam material. The articles are in a physical form capable of substantially completely encasing a victim with closure means attached to the article for ensuring the article retains the shape it assumes when the victim is encased thereby. The paragraphs which follow further describe the materials used in constructing the articles and various physical forms of the article especially adapted for its end use.

Passive rewarming articles of this invention are made with a closed-cell foam material. Such foam materials for use herein have a thermal conductivity of less than about 0.30 BTU/in./hr./°F./square ft. preferably ranging from about 0.20 to about 0.29 BTU/in./hr./°F./square ft. The closed-cell nature of the foam provides a barrier to outside air movement thereby ensuring the material's heat transfer characteristic is not substantially impaired by wind. Additionally, the closed-cell foam is an effective barrier to heat transfer under wet or dry conditions and is responsible for the aforementioned high excellent heat transfer characteristic. Quite often an accident victim is found with wet clothing resulting from over exposure to the elements, e.g. snow and rain. The fully dressed victim is placed on a blanket or other article which in a dry condition has good heat retention capability. However, the same article made with commonly used materials will have poor heat retention capability in the wet state. In fact, the environment's condition can be such that any water found in a victim's wet clothing will transfer to the outside of any rewarming article used where it will freeze.

The closed-cell foams used in the articles of this invention uniquely lend themselves particularly well to their end-use. That is, the close-cell foams do not absorb water to any appreciable extent. In effect, any water from the victim will remain close to the victim and will eventually be warmed by the body heat. The water and, most importantly, the heat in the water near the victim's body is not transferred through the closed-cell foam due to the foam's physical characteristics. The end result is that the overall transfer of heat from the victim through his wet clothing and closed-cell foam is substantially less than that experienced by other known materials tested under the same wet conditions.

Closed-cell foams also have other physical features which make them especially attractive for use herein. Thus, the closed-cell foams used in this invention are substantially non-absorbent and non-compressible. The result being the insulating characteristics of the rewarming article is not noticeably affected by a victim's body weight pressing against the foam and possibly the victim's emission of body fluids or presence of water. At the same time, the rewarming articles are readily cleaned of body fluids after use. The closed-cell foams are also flexible and drape well, two properties of immense value in a product of the type herein.

Examples of materials used in this invention include known polyethylene, cross-linked polyethylene, and polyvinylchloride/nitrile rubber, closed-cell foam materials. Especially preferred for use are the closed-cell cross-linked polyethylene and polyvinylchloride/nitrile rubber foams. One specific example of such a class of materials is Ensolite, available from Uniroyal, Inc.

Preferably, the foam material is about 0.10 inches to about 1.0 inches thick, more preferably about 0.10 inches to about 0.50 inches thick. Generally, the thickness of the foam is uniform throughout the entire rewarming article, though added insulation and comfort are achieved by having the portion of the head pocket made of a thicker foam, e.g. up to about 1.0 inches in thickness.

With reference to FIG. 1, there is shown a passive rewarming article having a body portion 11, side flaps 12 and 13, and foot flap 14. The body portion itself is sufficiently large to accommodate at least the torso of an adult victim when laid prone upon said body portion. Generally, it is rectangular in shape and ranges from about four feet to about seven feet in length and about two feet to about four feet in width. Extending from the body portion are at least one or, as shown in FIG. 1, two independent side flaps 12 and 13. Each of the side flaps operates independently and is foldable; that is, the flaps can be laterally folded back upon the body portion at seams 15. The purpose of the independent side flaps is that they permit ready access to only a portion of the body for medical attention if needed while the balance of the body remains covered by the other side flaps. This can be very important where a life-threatening situation exists.

Each flap can optionally have a closeable cover 16 over an opening. The purpose of the openings are to allow an attendant to gain access to the victim while the victim remains completely wrapped in the bag so as to perform any necessary medical functions which may be needed. The openings preferably range from about 10 square inches to about 180 square inches to allow ready access to the victim, but which, when covered by cover 16, do not permit the escape of body heat. Cover 16 is attached to the side flap by any conventional attachment means.

The flap 12 nearest to where a head pocket attaches to the body portion 11 has a generally curved-shaped, cut-out portion 17. The cut-out portion of the side flap is to accommodate the victim's head when said flap is folded over the victim. That is, the flap itself would not cover the victim's head. The portion removed from the corner of the side flap can be any shape, so long as it accommodates the victim's head when folded over.

The side flaps 12 and 13 can be an integral part of the body portion 11. However, for ease of construction they are generally produced separately and attached permanently to the body portion. For example, stitching or a heat seal can be used for attachment purposes. As shown in FIG. 1, a binding 18 is sewn onto the edges of the individual pieces of the article for strengthening purposes. The dimensions of the side flaps are such that together they extend the complete length of the body portion. Additionally, they are dimensioned so as to overlap with one another when folded laterally over the victim's body to ensure so that no open space remains through which body heat can escape. The exact dimensions of the side flaps 12 and 13 will depend on the dimensions of the body portion 11.

Attachment means are also provided on the side flaps to ensure that once folded over the victim they will remain in place during transport of the victim. Conventional tie-strings or preferably a a hook and loop attaching means known as Velcro is strategically placed on the side flaps to ensure the side flap's retention when properly folded. As shown in FIG. 1, Velcro strips 19 are attached along the inside edges on one set of side flaps and on the outside portions (not shown) of the opposite set of side flaps such that in operation the opposing Velcro strips mate. Such strips are very preferred because of their capability of attachment while an extraneous item, e.g. an intravenous tube extends through the strips and to the victim. Thus, the victim is completely encased by the article, yet is still accessable for limited functions. Preferably, the strips run in a generally horizontal direction on one set of side flaps and in a generally vertical direction on the opposite set of side flaps for ease of mating.

The foot flap 14 extends from one end of the body portion. It is dimensioned so that when folded longitudinally, it will completely cover the victim's feet and lower portions of his legs. The foot flap is generally rectangular in dimension. In a preferred embodiment, additional side flaps 20 are added to ensure that the victim's body is completely covered.

A disposable liner 21 is preferably used in the rewarming articles on the inside portion of the articles. The liner is made of an absorbent material, e.g. cellulose, cotton or wool. It is for the purpose of absorbing liquids, e.g. water from the victim's clothing or body fluids from the victim. This helps to ensure the insulating efficiency of the closed-cell foam is not impaired, aids in the victim's comfort, and provides a means to readily clean the rewarming article after use. The liner material is dimensioned to fit the various portions of the article. It is positioned prior to use and is readily removed and disposed of after use.

Head pocket 22 is provided for slipping over the victim's head so that it, together with the main part of the recovery bag, completely covers the victim. It can be large enough to accommodate head bandages, extrication collars, and neck braces. The head pocket is preferably detachable for ease of placement on the victim. Thus, the victim can be placed on the body portion of the recovery bag without particular regard to his exact placement. The head pocket 22 has a cutout 23 for exposing at least the victim's eyes. It can be larger so as to expose the victim's face. This cutout is merely to not unduly alarm the victim by completely encasing him in a darkened enclosure. The head pocket can be an integral piece of material properly dimensioned, but normally is fabricated from three or more pieces of material. Thus, side portions 24 and 25 are sewn to main portion 26 at seams 27. Attachment means such as Velcro strips 28 and 29 (shown in phantom in FIG. 2) are positioned on the inside of side portion 24 of the head pocket and on the outside of the side portion 25, respectively, of the head pocket.

In operation, the side portions 24 and 25 are opened when the victim's head is placed inside the head pocket. Next, side portion 25 is laid over the victim's head and side portion 24 is laid over side portion 25 with Velcro strips 28 and 29 mated to hold the side portions together. The head pocket has means by which it can be attached to the body portion of the recovery bag, for example, Velcro strips 30 and 31 can be strategically placed on the inside of the rewarming article and the outside, respectively, of the head pocket. Attaching the head pocket in this fashion provides some degree of head restraint.

Carrying straps are placed on the outside of the recovery bag for their obvious function of transporting a victim. The carrying straps (shown in FIG. 9) are made of any durable material which can be securely attached to the recovery bag, e.g. a 3,000 lb. test weight nylon strap.

FIG. 4 illustrates the construction of the material used in producing the rewarming article of this invention. Closed-cell foam 32 with fibrous backing 33 is shown. The fibrous backing 33 is used on the outside surface of the rewarming article in order to provide additional strength needed by the article, provide added toughness, and to act as an environmental barrier. Fibrous backings include materials which are separate from the foam or are embedded into the foam and are actually a part thereof. Woven fabric such as nylon and cotton are well known and useful herein. A neoprene coated nylon cloth is one example of a very useful backing. In a highly preferred embodiment of this invention, a disposable liner material 34 is also placed on the inside of the recovery bag. Such a liner material is for the purpose of absorbing or collecting water from a victim's clothing or body fluids which may be emitted from the victim. The disposable nature of the liner allows it to be removed once the victim is himself removed from the recovery bag. A new liner can readily be positioned in the recovery bag.

FIG. 5 illustrates another rewarming article of this invention wherein three side flaps 35, 36, and 37 on each side of body portion 38 are illustrated. The additional body flap allows more flexibility in wrapping the victim and subsequently transporting him. Each of the side flaps, when folded, overlap with one another; preferably, the middle side flap 36 overlaps the bottom and top side flaps when laterally folded. Foot flap 39 and side flaps 40 operate in the same manner as discussed above with reference to FIG. 1. Head pocket 41, as shown in FIG. 6, is similar in operation to the head pocket of FIGS. 2 and 3. Velcro strips 42 on the head pocket 41 are positioned in a generally verticle direction with strips 43 on body portion 38 positioned in a generally horizontal direction for ease of mating.

Passive rewarming articles with other physical shapes are also within the scope of this invention provided they are capable of substantially enclosing the victim's body and have closure means as aforedescribed. For example, the article can be generally rectangular in shape with attachment means in the form of a zipper or Velcro extending around the outer edges of three sides. When used, the victim is placed on one half, the second half folded thereover and the three sides secured together. A cut-out portion can be provided for accommodating the victim's head. Another article can be in the form of a pocket shape such that the victim is slipped into the article with attachment means on the open portion for enclosing the victim after being positioned there within.

Figure 8:
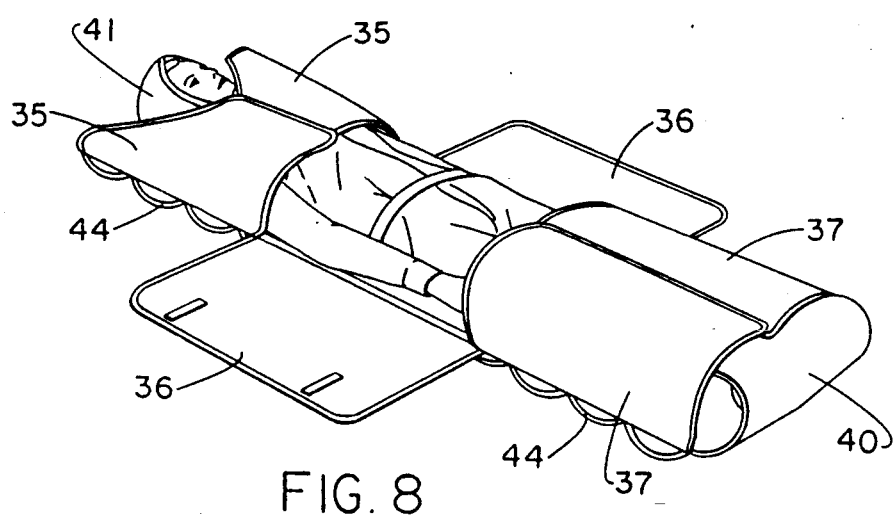
Figure 9:
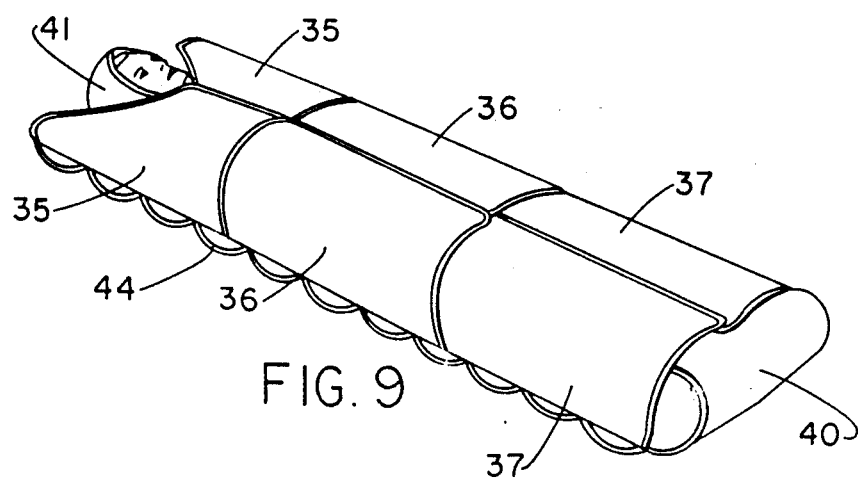

FIGS. 7-9 is schematic illustrations showing the use of the passive rewarming article of FIGS. 5 and 6. The head pocket 41 is usually first used by placing it over the victim's head so that at least his eyes are exposed by the cutout. The rewarming article is then placed adjacent to the victim in its fully opened position. As shown in FIG. 7, the victim is lifted onto the body portion 38 of the recovery bag. As shown in FIG. 8, the foot flap 40 is next folded over the feet and lower legs of the victim; side flaps 35 and 37 are folded laterally to ensure complete coverage of portions of the victim. Next, the middle side flap 36 is folded over the victim. The various attachment means are finally attached so to ensure that the various portions of the recovery bag remain in place. Carrying straps are used for transporting the victim. For example, a strap 44 is sewn along each of the outer edges of body portion 38 so as to form loops which act as handles. While not shown, provision can be made for use of a rigid backboard with the article for transporting a victim in a less limber fashion.

Figure 10:
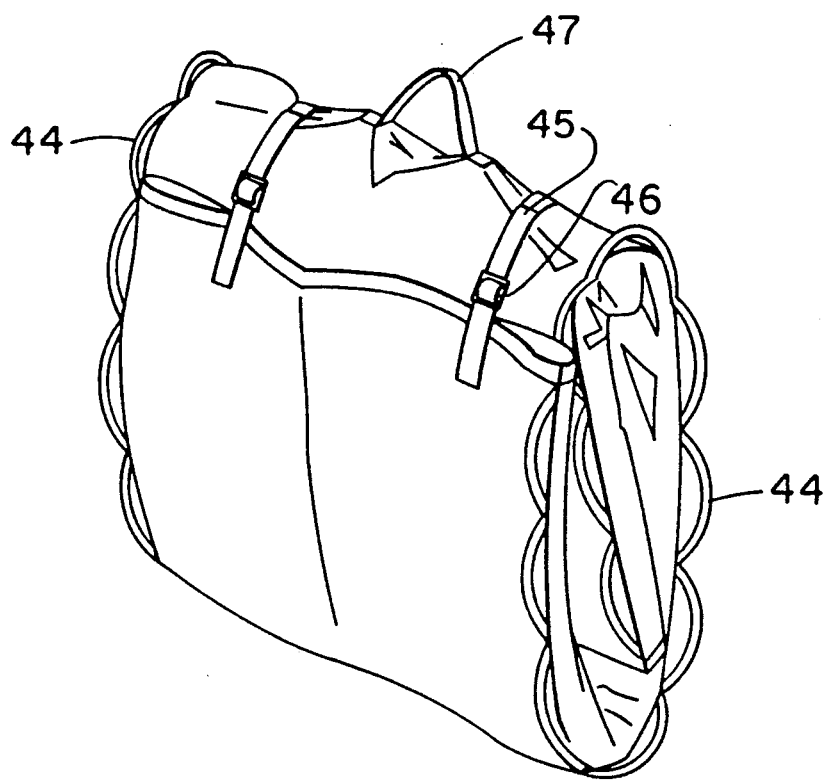
FIG. 10 is a view in perspective showing the rewarming article folded into a compact unit for easy carrying.

FIG. 10 shows the article of FIG. 5 in a folded configuration for ease of storage and portability. The side foot flaps 40 are initially folded inwardly and the foot flap 39 folded at the seam. Next, all side flaps 35-37 are folded inwardly at their seams. The article is now folded in thirds and held together by straps 45 and buckels 46 placed on the back side of the article. Handle 47 is provided for hand-carrying of the article. The resultant article is compact and easy to store and/or carry.

Figure 11:
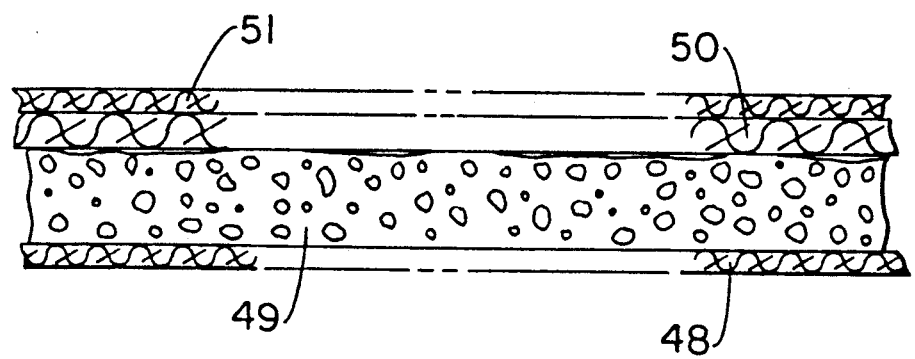
FIG. 11 is a partial cross section of the material construction used in making a preferred embodiment of the invention.

In FIG. 11, there is shown a partial cross section of certain materials used for constructing rewarming articles of another embodiment. The materials comprise fibrous backing 48, closed-cell foam material 49, sorbent lining 50 and disposable liner 51. The fibrous backing, closed-cell foam material, and disposable liner are the same materials and perform the same functions as described above with reference to FIG. 4. Sorbent lining 50 serves the function of drawing water away from the victim. Thus, in operation, water is drawn from the victim through the disposable liner 51 and into the sorbent lining 50. However, due to the closed-cell nature of the foam material 49, the water is not transported to the outside of the article. As a result the excellent heat transfer characteristics of the article is retained. Several water-sorbent materials such as natural and synthetic materials in the form of woven and non-woven mattings are useable. The sorbent material is generally not an integral part of the foam material, but is rather simply laid over the foam and adhered sufficiently to be held in place.

While the rewarming articles of this invention have been described with specific reference to the figures, it should be understood various other embodiments are within the scope of this invention.

What is claimed is:

1. A passive rewarming article for use with an accident victim under a wide range of environmental conditions, said article constructed from a closed-call foam material having a thermal conductivity of less than about 0.30 BTU/in./hr./°F./square ft. and ranging in thickness from about 0.10 inches to about 1.0 inches with a fibrous backing for adding strength and tear resistance to the article, further wherein the article is in a form capable of substantially completely encasing the victim with the closed-cell foam and having closure means permanently attached to the article for ensuring the article retains the shape it assumes when the victim is encased thereby.

2. The rewarming article of claim 1 wherein an opening is provided for exposing the victim's eyes.

3. The rewarming article of claim 1 wherein said article is comprised of a body portion with at least one independent side flap on each side of the body portion, and a foot flap, all of said flaps capable of folding inwardly to cover the victim.

4. A passive rewarming article for use with accident victims, said article constructed from a closed-cell foam material having a thermal conductivity of less than about 0.30 BTU/in./hr./°F./square ft. with a fibrous backing comprising:
   (a) a body portion made from the closed-cell foam sufficiently large to accommodate at least the torso of an adult victim when laid upon said body portion;
   (b) at least one independent side flap on each side of the body portion, said flaps made from the closed-cell foam and sufficiently large enough to laterally fold over and cover the victim's torso and upper legs;
   (c) a foot flap made from the closed-cell foam extending from a first end of the body portion sufficiently large enough to longitudinally fold over and cover the feet of the victim; and
   (d) a head pocket made from the closed-cell foam capable of attachment to the body portion at a second end, said head pocket dimensioned to slip over the victim's head and having a cut-out for exposing at least the victim's eyes.

5. The rewarming article of claim 4 wherein each side flap nearest where the head pocket attaches to the body portion has a portion removed from an upper corner to accommodate the victim's head when said flap is folded over the victim.

6. The rewarming article of claim 4 wherein there are three independent side flaps on each side of the body portion.

7. The rewarming article of claim 6 wherein said three independent side flaps on each side overlap, with a middle side flap overlapping adjacent side flaps when all three of said flaps are folded laterally over the victim.

8. The rewarming article of claim 4 wherein at least one of said side flaps has an opening allowing access to the victim for manipulation thereof.

9. The rewarming article of claim 4 further comprising attachment means to hold said side flaps in place.

10. The rewarming article of claim 9 wherein strips of hook and loop attaching means are properly positioned on the side flaps so as to cause said side flaps to attache to one another thereby enclosing the victim.

11. The rewarming article of claim 10 further comprising carrying straps attached to the article to permit ready movement of the victim.

12. The rewarming article of claim 4 wherein the fibrous backing is not an integral part of the foam material.

13. The rewarming article of claim 12 wherein the fibrous backing is neoprene coated nylon cloth.

14. The rewarming article of claim 12 further comprising a disposable liner material positioned on the closed cell foam so as to contact said victim when positioned on the article.

15. The rewarming article of claim 14 wherein the closed-cell foam has a thickness of from about 0.10 inches to about 1.0 inches.

16. The rewarming article of claim 15 wherein the closed-cell foam used in forming the body portion, side flaps and foot flap has a thickness ranging from about 0.10 inches to about 0.50 inches and the head pocket has a thickness ranging from about 0.10 inches to about 1.0 inches.

17. The rewarming article of claim 15 wherein the closed-cell foam has a thermal conductivity ranging from about 0.20 to about 0.29 BTU/in./hr./°F./square ft.

18. The rewarming article of claim 4 further comprising side flaps extending from the foot flap to ensure coverage of the victim's feet and legs.

19. The rewarming article of claim 4 further comprising a water-sorbent lining material positioned on the closed-cell foam material for drawing water away from the victim.

20. The rewarming article of claim 4 wherein the head pocket is detachable.

* * * * *